US010377738B2

(12) United States Patent
McGowan et al.

(10) Patent No.: US 10,377,738 B2
(45) Date of Patent: Aug. 13, 2019

(54) PYRIDONE DERIVATIVES FOR THE TREATMENT OF VIRAL INFECTIONS AND FURTHER DISEASES

(71) Applicant: JANSSEN SCIENCES IRELAND UNLIMITED COMPANY, Co Cork (IE)

(72) Inventors: David Craig McGowan, Brussels (BE); Pierre Jean-Marie Bernard Raboisson, Wavre (BE)

(73) Assignee: JANSSEN SCIENCES IRELAND UNLIMITED COMPANY, Ringaskiddy, Co Cork (IE)

( * ) Notice: Subject to any disclaimer, the term of this patent is extended or adjusted under 35 U.S.C. 154(b) by 0 days.

(21) Appl. No.: 14/892,701

(22) PCT Filed: May 23, 2014

(86) PCT No.: PCT/EP2014/060603
§ 371 (c)(1),
(2) Date: Nov. 20, 2015

(87) PCT Pub. No.: WO2014/187932
PCT Pub. Date: Nov. 27, 2014

(65) Prior Publication Data
US 2016/0108021 A1 Apr. 21, 2016

(30) Foreign Application Priority Data
May 24, 2013 (EP) .................... 13169076

(51) Int. Cl.
C07D 401/06 (2006.01)
(52) U.S. Cl.
CPC .................. C07D 401/06 (2013.01)
(58) Field of Classification Search
CPC .................................................. C07D 401/06
See application file for complete search history.

(56) References Cited

U.S. PATENT DOCUMENTS

| 6,028,076 | A  | 2/2000  | Hirota et al. |
| 6,329,381 | B1 | 12/2001 | Kurimoto et al. |
| 6,376,501 | B1 | 4/2002  | Isobe et al. |
| 6,458,798 | B1 | 10/2002 | Fujita et al. |
| 6,503,908 | B1 | 1/2003  | Maw |
| 6,583,148 | B1 | 6/2003  | Kelley et al. |
| 6,951,866 | B2 | 10/2005 | Fujita et al. |
| 7,030,118 | B2 | 4/2006  | Lombardo et al. |
| 7,091,232 | B2 | 8/2006  | Chow et al. |
| 7,498,409 | B2 | 3/2009  | Vlach et al. |
| 7,524,852 | B2 | 4/2009  | Arai et al. |
| 7,531,547 | B2 | 5/2009  | Dillon et al. |
| 7,754,728 | B2 | 7/2010  | Isobe et al. |
| 7,923,554 | B2 | 4/2011  | Hoornaert et al. |
| 8,012,964 | B2 | 9/2011  | Kurimoto et al. |
| 8,022,077 | B2 * | 9/2011 | Simmen ............. C07D 471/04 514/264.1 |
| 8,455,458 | B2 | 6/2013  | Marcum et al. |
| 8,486,952 | B2 | 7/2013  | Boy et al. |
| 8,637,525 | B2 | 1/2014  | Boy et al. |
| 8,916,575 | B2 | 12/2014 | McGowan et al. |
| 9,133,192 | B2 | 9/2015  | McGowan et al. |
| 9,284,304 | B2 | 3/2016  | McGowan et al. |
| 9,365,571 | B2 | 6/2016  | McGowan et al. |
| 9,376,448 | B2 | 6/2016  | Charifson et al. |
| 9,416,114 | B2 | 8/2016  | Gembus et al. |
| 9,422,250 | B2 | 8/2016  | Mc Gowan |
| 9,499,549 | B2 | 11/2016 | McGowan et al. |
| 9,556,176 | B2 | 1/2017  | Bonfanti et al. |
| 9,556,199 | B2 | 1/2017  | McGowan et al. |
| 9,598,378 | B2 | 3/2017  | McGowan et al. |
| 9,663,474 | B2 | 5/2017  | Last et al. |
| 9,878,996 | B2 | 1/2018  | Silverman et al. |
| 2005/0054590 | A1 | 3/2005 | Averett |
| 2006/0258682 | A1 | 11/2006 | Liao et al. |
| 2007/0225303 | A1 | 9/2007  | Ogita et al. |
| 2009/0285782 | A1 | 11/2009 | Gao et al. |
| 2010/0143299 | A1 | 6/2010  | Gao et al. |
| 2014/0148433 | A1 | 5/2014  | Follmann et al. |
| 2015/0274676 | A1 | 10/2015 | McGowan et al. |
| 2015/0299221 | A1 | 10/2015 | Bonfanti et al. |
| 2015/0336907 | A1 | 11/2015 | Gembus et al. |
| 2016/0304531 | A1 | 10/2016 | Bonfanti et al. |

FOREIGN PATENT DOCUMENTS

| CN | 101784548 A | 7/2010 |
| EP | 0882727 | 12/1998 |
| EP | 0899263 A3 | 3/1999 |
| EP | 1552842 A1 | 6/2003 |
| EP | 1110951 A1 | 6/2006 |
| EP | 1939198 A1 | 7/2008 |

(Continued)

OTHER PUBLICATIONS

Extended European Search Report for European Application EP13169076.0 Mailed Sep. 10, 2013.
International Search Report mailed Jul. 15, 2014 for Application No. PCT/EP2014/060603.
Baraldi, P., et al., "New Strategies for the Synthesis of A₃ Adenosine Receptor Antagonists", Bioorganic & Medicinal Chemistry, vol. 11, pp. 4161-4169 (2003).
Bell, L., et al., "Chemistry of 5-Pyrimidinecarboxaldehydes", J. Heterocyclic Chemistry, vol. 29, pp. 41-44 (2003).
Hoffmann, Jules A., "The Immune Response of *Drosophila*", Nature, vol. 426, pp. 33-38 (2003).
Mesguiche, V., et al., "4-Alkoxy-2,6-diaminopyrimidine Derivatives: Inhibitors of Cyclin Dependent Kinases 1 and 2", Bioorganic & Medicinal Chemistry Letters, vol. 13, pp. 217-222 (2003).
Takeda, K., et al., "Toll-Like Receptors", Annual Rev. Immunology, vol. 21, pp. 335-376 (2003).

(Continued)

Primary Examiner — Alexander R Pagano
Assistant Examiner — Ebenezer O Sackey
(74) Attorney, Agent, or Firm — Brian C. Trinque; Lathrop Gage LLP

(57) ABSTRACT

This invention relates to pyridone derivatives, processes for their preparation, phamaceutical compositions, and their use in therapy.

33 Claims, No Drawings
Specification includes a Sequence Listing.

(56) References Cited

FOREIGN PATENT DOCUMENTS

| EP | 1970373 A1 | 9/2008 |
|---|---|---|
| EP | 2133353 A1 | 12/2009 |
| EP | 2138497 A1 | 12/2009 |
| JP | 64063582 | 3/1989 |
| JP | 2000053653 | 2/2000 |
| JP | 2000053654 | 2/2000 |
| JP | 2008222557 A | 9/2008 |
| JP | 2009528989 A | 8/2009 |
| JP | 2010522151 A | 7/2010 |
| JP | 2010532353 A | 10/2010 |
| WO | WO 98/01448 A1 | 1/1998 |
| WO | 199808847 A1 | 3/1998 |
| WO | 199814448 A1 | 4/1998 |
| WO | 199850370 A1 | 11/1998 |
| WO | WO 99/28321 A1 | 6/1999 |
| WO | 199932122 A1 | 7/1999 |
| WO | 199940091 A1 | 8/1999 |
| WO | 199941253 A1 | 8/1999 |
| WO | 200006577 A1 | 2/2000 |
| WO | 200061562 A1 | 10/2000 |
| WO | 2002087513 A2 | 11/2002 |
| WO | 2002088080 A2 | 11/2002 |
| WO | 2003055890 A1 | 7/2003 |
| WO | 2004029054 A1 | 8/2004 |
| WO | 2005007672 A2 | 1/2005 |
| WO | 2005092892 A1 | 10/2005 |
| WO | 2005092893 A1 | 10/2005 |
| WO | 2006015985 A1 | 2/2006 |
| WO | 2006050843 A1 | 5/2006 |
| WO | 2006120252 A2 | 11/2006 |
| WO | WO 2006/117670 A1 | 11/2006 |
| WO | 2007034881 A1 | 3/2007 |
| WO | 2007056208 A1 | 5/2007 |
| WO | 2007063934 A1 | 6/2007 |
| WO | 2007084413 A2 | 7/2007 |
| WO | 2007093901 A1 | 8/2007 |
| WO | 2008009078 A2 | 1/2008 |
| WO | 2008073785 A2 | 6/2008 |
| WO | 2008075103 A1 | 6/2008 |
| WO | 2008114008 A1 | 9/2008 |
| WO | 2008114817 A1 | 9/2008 |
| WO | 2008114819 A1 | 9/2008 |
| WO | 2008115319 A2 | 9/2008 |
| WO | 2008147697 A1 | 12/2008 |
| WO | 2009005687 A1 | 1/2009 |
| WO | 2009023179 A2 | 2/2009 |
| WO | 2009030998 A1 | 3/2009 |
| WO | WO 2009/067081 A1 | 5/2009 |
| WO | 2009080836 A2 | 7/2009 |
| WO | 2009099650 A2 | 8/2009 |
| WO | WO2009032668 A3 | 9/2009 |
| WO | 2009134624 A1 | 11/2009 |
| WO | 2009157560 A1 | 12/2009 |
| WO | 2010006025 A1 | 1/2010 |
| WO | WO 2010/007116 A2 | 1/2010 |
| WO | 2010133885 A1 | 11/2010 |
| WO | 2011014535 A1 | 2/2011 |
| WO | 2011049825 A1 | 4/2011 |
| WO | 2011049987 | 4/2011 |
| WO | 2011062253 A1 | 5/2011 |
| WO | 2011062372 A3 | 5/2011 |
| WO | 2012066335 A1 | 5/2012 |
| WO | 2012067269 A1 | 5/2012 |
| WO | 2012136834 | 10/2012 |
| WO | 2012156498 A1 | 11/2012 |
| WO | 2013068438 A1 | 5/2013 |
| WO | 2013117615 A1 | 8/2013 |
| WO | 2014053595 A1 | 4/2014 |

OTHER PUBLICATIONS

Ulevich, R., et al., "Therapeutics Targeting the Innate Immune System", Nature, vol. 4, pp. 512-520.

Abdillahi, et al., "Synthesis of a Novel Series of Thieno[3,2-d]pyrimidin-4-(3H)-ones", Synthesis, vol., 9: pp. 1423-1430 (2010).
Banker (Editor), "Prodrugs", Modern Pharmaceutics, Third Edition: pp. 596 (1976).
Barker, et al., "A Rapid Conversion of 3-Oxothiolanes into 3-Aminothiophenes", Synthetic Communications, vol. 32(16): pp. 2565-2568 (2002).
Bennet, et al. (Editor), "Part XIV Oncology", Cecil Textbook of Medicine, vol. 1, 20th Edition: pp. 1004-1010 (1996).
Brittain, et al., "Effects of Pharmaceutical Processing on Drug Polymorphs and Solvates", Polymorphism in Pharmaceutical Solids, 1999, pp. 331-360, Chapter 8.
Bruns, et al, "Solubilities of Adenosine Antagonists Determined by Radioreceptor Assay", Journal of Pharmacy and Pharmacology, vol. 41: pp. 590-594 (1989).
Chawla, et al., "Challenges in Polymorphism of Pharmaceuticals", Current Research & Information on Pharmaceutical Sciences, vol. 5(1): pp. 9-12 (Jan.-Mar. 2004).
De Clercq, et al., "(S)-9-(2,3-Dihydroxypropyl)adenine: An Aliphatic Nucleoside Analaog With Broad-Spectrum Antiviral Activity", Science, 1978, pp. 563-565, vol. 200.
De Nardo, "Toll-Like Receptors: Activation, Signalling and Transcriptional Modulation", Cytokine, 2015, pp. 181-189, vol. 74.
Dermer, "Another Anniversary for the War on Cancer", Bio/Technology, vol. 12: pp. 320 (Mar. 1994).
Douglas, Jr., "Introduction of Viral Diseases", Cecil Textbook of Medicine, 20th Edition, vol. 2: pp. 1973-42 (1996).
Freshney, et al., "Culture of Animal Cells", Manual of Basic Technique, 1983, pp. 1-6, Chapter 1.
Fried, et al., "Peginterferon Alfa-2a Plus Ribavirin for Chronic Hepatitis C Virus Infection", New England Journal of Medicine, Sep. 26, 2002, pp. 975-985, vol. 347 (13).
Grimm, et al., "Toll-like receptor (TLR) 7 and TLR8 expression on CD133+ cells in colorectal cancer points to a specific roid for inflammation inducted TLRs in tumourigenesis and tumour progression", European Journal of Cancer, 2010, pp. 2849-2857, vol. 46.
Hackam, et al, "Translation of Research Evidence From animals to Humans", JAMA, vol. 296 (14): pp. 1731-1732 (2006).
Hood, et al., "Immunoprofiling toll-like receptor ligands Comparison of Immunostimulatory and proinflammatory profiles in ex vivo human blood models", Human Vaccines, vol. 6(4): pp. 322-335 (Apr. 2010).
Horscroft, et al., "Antiviral applications of toll-like receptor agonists", J. Antimicrob. Chemother., pp. 1-13 (Jan. 18, 2016).
Huddleston, et al., "A Convenient Synthesis of 2-Substituted 3-Hydroxy- and 3-Amino-Thiophens From Derivatives of 2-Choroacrylic Acid", Synthetic Communications, vol. 9(8): pp. 731-734 (1979).
Isobe, et al., "Synthesis and Structure-Activity Relationships of 2-Substituted-8-hydroxyadenine Derivatives as Orally Available Interferon Inducers Without Emetic Side Effects", Bioorganic & Medicinal Chemistry, vol. 11: pp. 3641-3647, (2003).
Jiang, et al., "Synthesis of 4-chlorothieno[3,2-d]pyrimidine", Chemical Industry and Engineering Progress, vol. 30: pp. 2532-35, (2011). [Wth English Abstract].
Jordan, "Tamoxifen: A Most Unlikely Pioneering Medicine", Nature Reviews, vol. 2: pp. 205-213, (Mar. 2003).
Kanzler, et al., "Therapeutic Targeting of Innate Immunity With Toll-Like Receptor Agonists and Antagonists", Nature Medicine, vol. 13(5): pp. 552-559 (May 2007).
Krieger, et al, Enhancement of Hepatitis C Virus RNA Replication by Cell Culture, Journal of Virology, May 1, 2001, 4614-1624, 75-10, DE.
Kurimoto, et al., "Synthesis and Structure—Activity Relationships of 2-Amino-8-hydroxyadenines as Orally Active Interferon Inducing Agents", Bioorganic & Medicinal Chemistry, vol. 11: pp. 5501-5508 (2003).
Liu, et al., "Synthesis and Biological Activity of 3-and 5-Amino Derivatives of Pyridine-2Carboxaldehyde Thiosemicarbazone", J. Med. Chem, Vo. 39: pp. 2586-2593 (1996).
Lohmann et al, Viral and Cellular Determinants of Hepatitis C Virus RNA Replication in Cell Culture, Journal of Virology, vol. 77(5): pp. 3007-3019 (Mar. 2003).

(56) References Cited

OTHER PUBLICATIONS

Lohmann, et al., Replication of Subgenomic Hepatitis C Virus RNAs in a Hepatoma Cell Line, Science, 1999, pp. 110-113, vol. 285.
Makkouk et al., "The potential use of Toll-Like Receptors (TLR) agonistd and antagonists as prophylactic and/or therapeutic agents", Immunopharrnacology and Immunotoxicology, vol. 31(3): pp. 331-338 (2009).
Moreau, et al., "Synthesis of cyclic adenosine 5'-diphosphate ribose analogues: a C2' endo/syn "southern" ribose conformation underlies activity at the sea urchin cADPR receptor", Organic & Biomolecular Chemistry, vol. 9: pp. 278-290 (2011).
Musmuca, et al, "Small-Molecule Interferon Inducers. Toward the Comprehension of the Molecular Determinants through Ligand-Based Approaches", J. Chem. Inf. Model., vol. 49: pp. 1777-1786 (2009).
Newman, et al., "Solid-State Analysis of the Active Pharmaceutical Ingredient in Drug Products", Drug Discovery Today, Oct. 19, 2003, pp. 898-905, vol. 8(19).
O'Hara, et al., "Regioselective Synthesis of imidazo[4,5-g] guinazoline Quinone Nucleosides and Quinazoline Amino Nucleosides. Studies of their Xanthine Oxidase and Purine Nucleoside Phosphorylase Substrate Activity", J. Org. Chem. vol. 56: pp. 776-785 (1991).
Ohto, et al., "Structure and Function of Toll-Like Receptor 8", Microbes and Infections, vol. 16: pp. 273-282 (2014).
Thomas, et al., "Investigating Toll-Like Receptor Agonists for Potential to Treat Hepatitis C Virus Infection", Antimicrobial Agents and Chemotherapy, vol. 51(3): pp. 2969-2978 (Aug. 2007).
Tran, et al, "Design and optimization of orally active TLR7 agonists for the treatment of hepatitis C virus infection", Bioorganic & Medicinal Chemistry Letters, vol. 21: pp. 2389-2393 (2011).
Ulrich, et al, "Crystallization", Kirk-Othmer Encyclopedia of Chemical Technology, Chapter 4: pp. 1-63, (Aug. 16, 2002).
Vedantham, et al., "Mechanism of Interferon Action in Hairy Cell Leukemia: a Model of Effective Cancer Biotherapy", Cancer Research, vol. 52: pp. 1056-1066 (Mar. 1, 1992).
Vippagunta, et al., "Crystalline Solids", Advance Drug Delivery Reviews, vol. 48: pp. 3-26 (2001).
Warshakoon, et al., "Potential Adjuvantic Properties of Innate Immune Stimuli", Human Vaccines, vol. 5(6): pp. 381-394 (Jun. 2009).
Wermuth, "Molecular Variations Based on Isosteric Replacements", The Practice of Medicinal Chemistry, 1996, pp. 203-237, Ch. 13.
Wolff, et al, Burger's Medicinal Chemistry and Drug Discovery, -, 1994, pp. 975-977, 5th Edition, vol. 1.
Yin, et al., "Synthesis of 2,4-Diaminoquinazolines and Tricyclic Quinazolines by Cascade Reductive Cyclization of Methyl N-Cyano-2-nitrobenzimidates", J. Org. Chem., vol. 77: pp. 2649-2658 (2012).
Yu, et al, "Toll-Like Receptor 7 Agonists: Chemical Feature Based", PLOS ONE, vol. 8 (3): pp. 1-11 e56514, (Mar. 20, 2013).
Yu, et al., "Dual Character of Toll-Like Receptor Signaling: Pro-Tumorigenic Effects and Anti-Tumor Functions", Biochimica et Biophysica Acta, vol. 1835: pp. 144-154 (2013).
Zhao, et al., "Toll-Like Receptors and Prostate Cancer", Frontiers in Immunology, vol. 5 (Article 352): pp. 1-7 (Jul. 2014).
International Search Report for Corresponding Application No. PCT/EP2012/059234, dated Nov. 18, 2013.
Extended European Search Report for Corresponding Application No. EP11166538.6, dated Nov. 22, 2011.
International Search Report for Corresponding Application No. PCT/EP2012/072090, dated Jan. 4, 2013.
International Search Report for Corresponding Application No. PCT/EP2013/052372 , dated Apr. 17, 2013.
International Search Report for Corresponding Application No. PCT/EP2013/064763, dated Aug. 3, 2013.
International Search Report for Corresponding Application No. PCT/EP2013/066673, dated Sep. 6, 2013.
International Search Report for Corresponding Application No. PCT/EP2013/070990, dated Jan. 17, 2014.
International Search Report for Corresponding Application No. PCT/EP2013/070488, dated Nov. 14, 2013.
International Search Report for Corresponding Application No. PCT/EP2013/073901, dated Dec. 16, 2013.
International Search Report for Corresponding Application No. PCT/EP2014/053273, dated Mar. 18, 2014.
International Search Report for Corresponding Application No. PCT/EP2014/056270, dated Jul. 21, 2014.
International Search Report for Corresponding Application No. PCT/EP2014/063467, dated Nov. 3, 2014.
International Search Report for Corresponding Application No. PCT/EP2014/066219, dated Nov. 13, 2014.
Isobe, et al., "Synthesis and Biological Evaluation of Novel 9-Substituted-8-Hydroxyadenine Derivatives as Potent Inferferon Inducers", J. Med. Chem., vol. 49; pp. 2088-2095 (2006).
Jurk, et al., "Human TLR7 or TLR8 Independently Confer Responsiveness to the Antiviral Compound R-848", Nature Immunology, Jun. 2002, pp. 499, vol. 3 (6).
Kurimoto, et al., "Synthesis and Evaluation of 2-Substituted 8-Hydroxyadenines as Potent Interferon Inducers with Improved Oral Bioavailabilities", Bioorganic & Medicinal Chemistry, vol. 12; pp. 1091-1099 (2004).
Lee, et al., "Activation of Anti-Hepatitis C Virus Responses via Toll-Like Receptor 7", PNAS, vol. 3 (6); pp. 1828-1833 (Feb. 7, 2006).
Roethle, et al., "Identification and Optimization of Pteridinone Toll-Like Receptor 7 (TLR7) Agonists for the Oral Treatment of Viral Hepatitis", Journal of Medicinal Chemistry, vol. 56; pp. 7324-73333 (2013).
Bizanek, et al., "Isolation and Structure of an Intrastrand Cross-Link Adduct of Mitomycin C nd DNA", Biochemistry, 1992, pp. 3084-3091, vol. 31.
McGowan et al., "Novel Pyrimidine Toll-Like Receptor 7 and 8 Dual Agonists to Treat Hepatitis B Virus", Journal of Medicinal Chemistry, 2016, pp. 7936-7949, vol. 59 No. 17.
Organic Syntheses Collective, "3-Methylcoumarone", Organic Syntheses Collective, 1963, pp. 43-46, vol. 4.
Tomonori, et al., "Ti-Crossed-Claisen Condensation between Carboxylic Ester and Acid Chlorides or Acids: a Highly Selective and General Method for the Preparation of Various β-Keto Esters", Journal of the American Chemical Society, vol. 127:pp. 2854-55 (2005).

\* cited by examiner

PYRIDONE DERIVATIVES FOR THE TREATMENT OF VIRAL INFECTIONS AND FURTHER DISEASES

CROSS-REFERENCE TO RELATED APPLICATIONS

This application is the national stage filing under USC 371 of international application PCT/EP2014/060603 filed on May 23, 2014, which claims priority to European Patent Application No. 13169076.0 filed 24 May 2013, the complete disclosures of which are hereby incorporated herein by reference for all purposes.

SEQUENCE LISTING

The instant application contains a Sequence Listing which has been submitted electronically in ASCII format and is hereby incorporated by reference in its entirety. Said ASCII copy, created on Feb. 3, 2017, is named TIP0299USPCT_SL.txt and is 563 bytes in size.

This invention relates to pyridone derivatives, processes for their preparation, pharmaceutical compositions, and their use in therapy.

The present invention relates to the use of pyridone derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named simply TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For detailed reviews on toll-like receptors see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as purine derivatives in WO 2006 117670, adenine derivatives in WO 98/01448 and WO 99/28321, and pyrimidines in WO 2009/067081.

However, there exists a strong need for novel Toll-Like receptor modulators having preferred selectivity, and an improved safety profile compared to the compounds of the prior art.

In accordance with the present invention a compound of formula (I) is provided

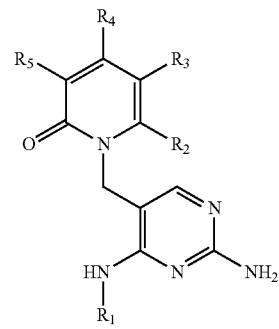

or a pharmaceutically acceptable salt, solvate or polymorph thereof, wherein $R_1$ is $C_{1-6}$ alkyl, optionally substituted by one or more substituents independently selected from aryl, halogen, hydroxyl, amino, carboxylic acid, carboxylic ester, carboxylic amide, acyl sulfonamide, $C_{1-3}$ alkyl, $C_{3-6}$ cycloalkyl, sulfone, sulfoxide, sulfonamide, heterocycle or nitrile;

$R_2$, $R_3$, $R_4$, and $R_5$ are independently selected from hydrogen, halogen, $C_{1-3}$ alkyl, $C_{1-3}$ alkoxy, $C_{3-6}$ cycloalkyl, aryl, —$CF_3$ or heterocycle;

or wherein $R_2$ is fused with $R_3$ to form a ring structure, $R_3$ is fused with $R_4$ to form a ring structure or $R_4$ is fused with $R_5$ to form a ring structure.

In a first embodiment the present invention provides compounds of formula (I) wherein $R_1$ is n-butyl and wherein $R_2$, $R_3$, $R_4$, and $R_5$ are hydrogen.

In a further embodiment the current invention relates to compounds of formula (I) wherein $R_1$ is n-butyl and wherein $R_2$ is fused with $R_3$ to form a ring structure, $R_3$ is fused with $R_4$ to form a ring structure or $R_4$ is fused with $R_5$ to form a ring structure.

The compounds of formula (I) and their pharmaceutically acceptable salt, solvate or polymorph thereof have activity as pharmaceuticals, in particular as modulators of Toll-Like Receptor TLR7 and/or TLR8 activity especially TLR7 activity.

In a further aspect the present invention provides a pharmaceutical composition comprising a compound of formula (I) or a pharmaceutically acceptable salt, solvate or polymorph thereof together with one or more pharmaceutically acceptable excipients, diluents or carriers.

Furthermore a compound of formula (I) or a pharmaceutically acceptable salt, solvate or polymorph thereof according to the current invention, or a pharmaceutical composition comprising said compound of formula (I) or a pharmaceutically acceptable salt, solvate or polymorph thereof can be used as a medicament.

Another aspect of the invention is that a compound of formula (I) or a pharmaceutically acceptable salt, solvate or polymorph thereof, or said pharmaceutical composition comprising said compound of formula (I) or a pharmaceutically acceptable salt, solvate or polymorph thereof can be used accordingly in the treatment of any disorder in which the modulation of TLR7 and/or TLR8 is involved.

The term "alkyl" refers to a straight-chain or branched-chain saturated aliphatic hydrocarbon containing the specified number of carbon atoms.

The term "halogen" refers to fluorine, chlorine, bromine or iodine.

The term "cycloalkyl" refers to a carbocyclic ring containing the specified number of carbon atoms.

The term "alkoxy" refers to an alkyl (carbon and hydrogen chain) group singular bonded to oxygen like for instance a methoxy group or ethoxy group.

The term "aryl" means an aromatic ring structure optionally comprising one or two heteroatoms selected from N, O and S, in particular from N and O. Said aromatic ring structure may have 5, 6 or 7 ring atoms. In particular, said aromatic ring structure may have 5 or 6 ring atoms.

The term "heterocycle" refers to molecules that are saturated or partially saturated and include ethyloxide, tetrahydrofuran, dioxane or other cyclic ethers. Heterocycles containing nitrogen include, for example azetidine, morpholine, piperidine, piperazine, pyrrolidine, and the like. Other heterocycles include, for example, thiomorpholine, dioxolinyl, and cyclic sulfones.

The term "ring structure" means a 5-7 membered, preferably 6-membered, saturated or partially saturated monocyclic moiety optionally comprising one or more heteroatoms selected from nitrogen, oxygen or sulfur.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

PREPARATION OF COMPOUNDS

Compounds of formula (I) are prepared according to scheme 1.

Scheme 1 (where preparation of 1 is shown as an example):

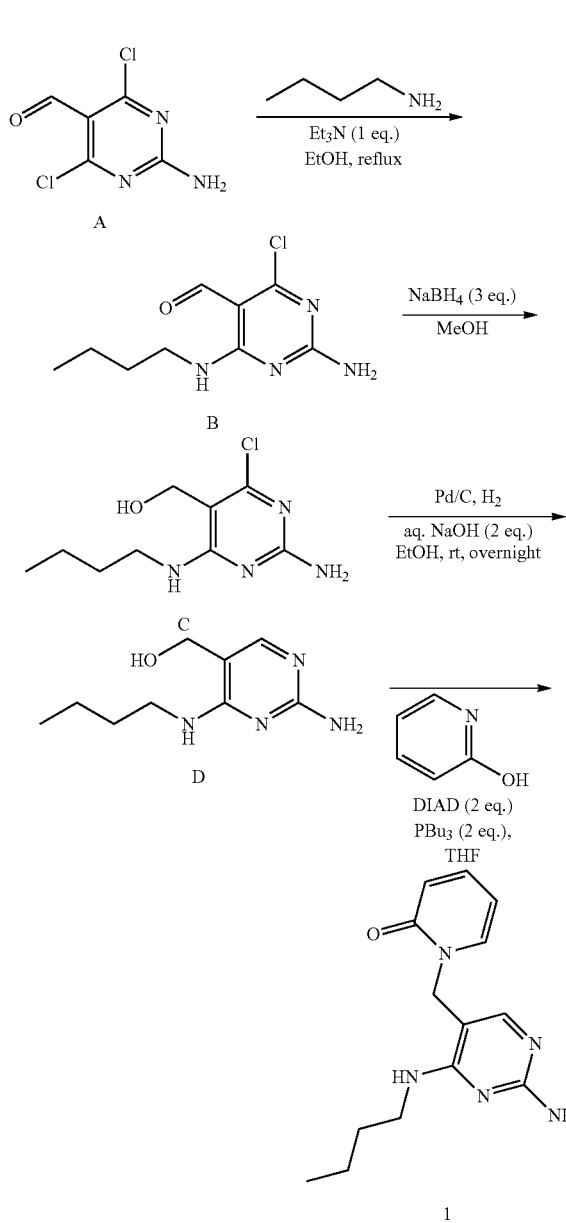

Compounds of type A in scheme 1 can be functionalized with amines under thermal conditions in a polar solvent, for example ethanol, with or without a base (e.g. triethylamine). The aldehyde group of B can be converted to the alcohol via a reducing agent like NaBH4 in a polar solvent (e.g. methanol). The chlorine in compounds of type C can be removed using Pd/C under a hydrogen atmosphere and basic conditions. The alcohol group is then functionalized under standard mitsunobu conditions to afford the pyridone final products.

The preparation of intermediates A and B is described in the literature (Bioorganic and Medicinal Chemistry 11, 2003, p 4161; J. Heterocyclic Chem., 20, 41 (1983); Bioorganic and Medicinal Chemistry Letters 13 (2003) p 217).

Preparation of B

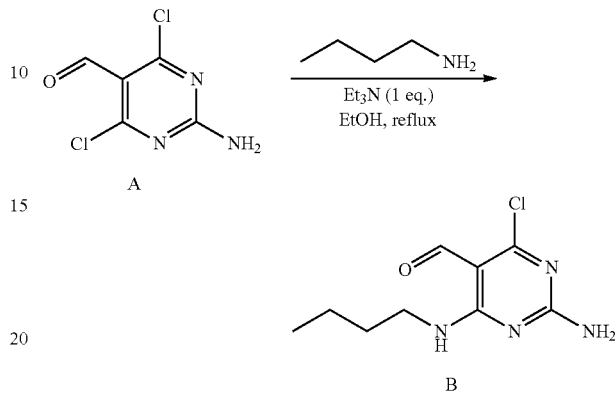

A (10.0 g, 52.08 mmol) was added in ethanol (100 mL) then n-butylamine (3.81 g, 52.08 mmol) and triethylamine (5.27 g, 52.08 mmol) were added to the solution. The mixture was heated to reflux for 8 hours. The solution was allowed to reach to 0° C. and the solid was isolated via filtration and washed with ethanol then dried under vacuum to afford B (10 g).

LC-MS m/z=229 (M+H); 1.20 min $^1$H NMR (400 MHz, d-Chloroform) δ ppm 0.95 (t, 3H), 1.31-1.42 (m, 2H), 1.53-1.65 (m, 2H), 3.40-3.50 (m, 2H), 5.11 (br. s., 2H), 9.22 (br. s., 1H), 10.07 (s, 1H)

Preparation of C

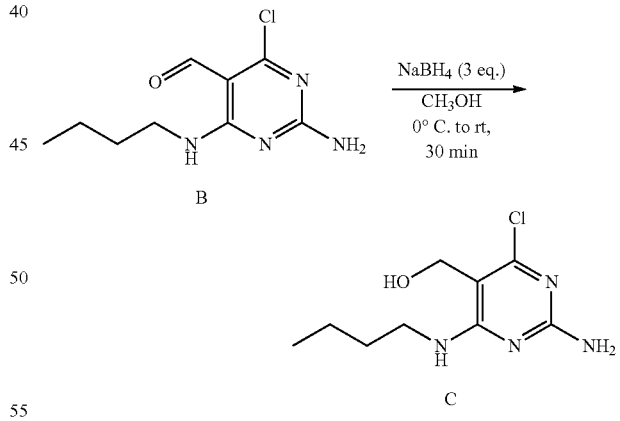

NaBH$_4$ (4 g, 105.73 mmol) was added in small portions to a mixture of B (8.0 g, 35 mmol) in methanol at 0° C. The mixture was stirred at room temperature for 30 minutes. The mixture was treated with saturated NaHCO$_3$ (100 mL) and H$_2$O (100 mL) slowly at 0° C., then stirred at room temperature for 10 min. The precipitate was isolated by filtration and washed with water (50 mL) and ethyl acetate: methyl t-butyl ether (1:5). The filtrate was extracted with ethyl acetate (2×200 mL). The combined organic layers were washed with brine, dried (Na$_2$SO$_4$), the solids were removed by filtration and the solvent of the filtrate was removed under reduced pressure. The residue was treated with ethyl acetate: methyl t-butyl ether (1:5). The precipitate was isolated by filtration and washed with methyl t-butyl ether. The precipitates were combined and dried (vacuum, 50° C., 30 minutes) to afford C.

LC-MS m/z=231 (M+H), 0.90 min $^1$H NMR (400 MHz, DMSO-d$_6$) δ ppm 0.90 (t, 3H), 1.31 (m, 2H), 1.50 (m, 2H), 3.28 (m, 2H), 4.4 (m, 2H), 4.92 (m, 1H), 6.29 (br. s., 2H), 6.55 (m, 1H)

Preparation of D

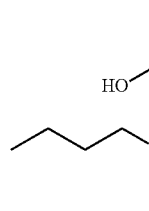

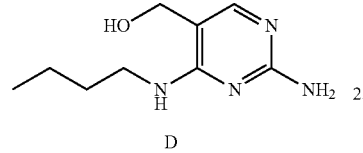

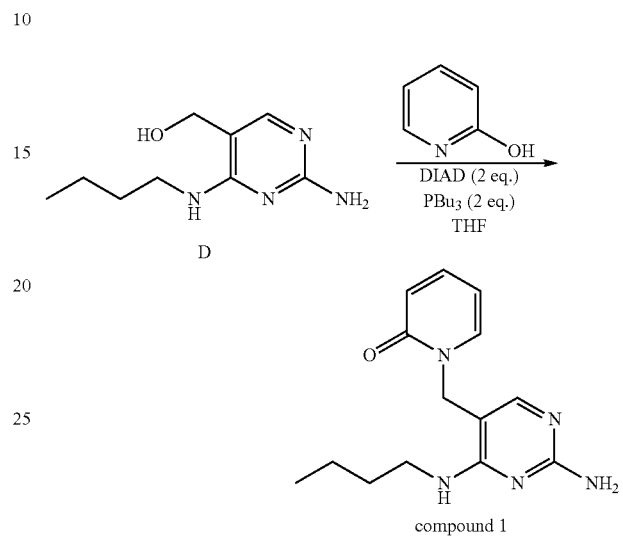

A solution of NaOH (1.6 g, 40 mmol) in H$_2$O (5 mL) was added to a solution of C (5.8 g, 21.37 mmol, purity 85%) in ethanol (150 mL) at room temperature. To this was added 10% Pd/C (0.6 g). The flask was sealed and exposed to hydrogen gas for 15 hours. The hydrogen gas was removed and replaced with nitrogen, the catalyst was removed by filtration, and the solvent of the filtrate was removed under reduced pressure. Ethyl acetate was added and the mixture was washed with H$_2$O, brine, dried (Na$_2$SO$_4$). The solids were removed via filtration and the solvent of the filtrate was removed under reduced presssure. The residue was washed with methyl t-butyl ether. The precipitate was isolated by filtration and washed with methyl t-butyl ether. The solid was collected and dried (vacuum, 50° C., 30 minutes) to afford D.

LC-MS m/z=197 (M+H); 3.21 min $^1$H NMR (400 MHz, DMSO-d$_6$) δ ppm 0.90 (t, J=7.4 Hz, 3H), 1.24-1.41 (m, 2H), 1.41-1.59 (m, 2H), 3.23-3.34 (m, 2H), 4.21 (br. s., 2H), 4.85 (br. s., 1H), 5.87 (s, 2H), 6.19 (t, J=5.3 Hz, 1H), 7.50 (s, 1H)

Preparation of Compound 1

DIAD (1.3 g, 6.429 mmol) was added to a mixture of D (0.5 g, 2.29 mmol, purity 90%), 2-hydroxypyridine (0.326 g, 3.43 mmol) and tributylphosphine (1.34 g, 6.62 mmol) in anhydrous THF (10 mL) at 0° C. under N$_2$ atmosphere. The mixture was stirred at room temperature overnight and then refluxed for 3 h. The mixture was evaporated under vacuum. The residue was treated with petroleum ether: methyl t-butyl ether (1:1). The mixture was evaporated under reduced pressure. Methyl t-butyl ether was added. The mixture was stirred at 0° C. for 20 min. The precipitate was isolated by filtration and washed with methyl t-butyl ether. The solid was collected and dried (vacuum, 50° C., 30 minutes) to afford 1.

TABLE 1

Compounds of formula (I).

| Co. No. | STRUCTURE | H NMR | LC Method, Rt (minutes) |
|---|---|---|---|
| 1 | 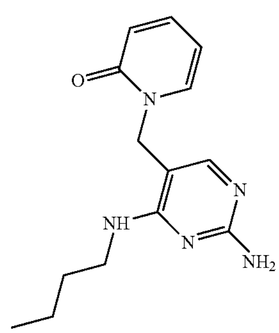 [SMILES: CCCCNc1nc(N)ncc1Cn1ccccc1=O] | $^1$H NMR (400 MHz, DMSO-d$_6$) δ ppm 0.85 (t, J = 7.4 Hz, 3 H), 1.26 (dq, J = 15.0, 7.3 Hz, 2 H), 1.44 (quin, J = 7.2 Hz, 2 H), 3.19-3.27 (m, 2 H), 4.79 (s, 2 H), 6.02 (s, 2 H), 6.33 (td, J = 6.7, 1.3 Hz, 1 H), 6.48 (d, J = 8.8 Hz, 1 H), 7.30 (t, J = 5.0 Hz, 1 H), 7.45 (ddd, J = 9.0, 6.8, 2.0 Hz, 1 H), 7.74 (dd, J = 6.8, 1.5 Hz, 1 H), 7.85 (s, 1 H) | A, 3.77 |

TABLE 1-continued

Compounds of formula (I).

| Co. No. | STRUCTURE | H NMR | LC Method, Rt (minutes) |
|---|---|---|---|
| 2 | 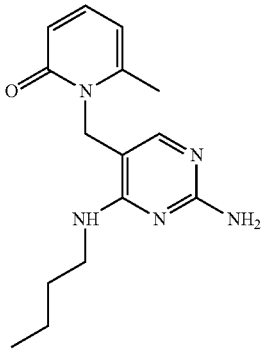 [SMILES: CCCCNc1nc(N)ncc1Cn1c(C)cccc1=O] | $^1$H NMR (400 MHz, METHANOL-$d_4$) δ ppm 0.94 (t, J = 7.3 Hz, 3 H), 1.29-1.42 (m, 2 H), 1.62 (quin, J = 7.3 Hz, 2 H), 2.51 (s, 3 H), 3.52 (t, J = 6.9 Hz, 2 H), 5.18 (s, 2 H), 6.43 (d, J = 6.8 Hz, 1 H), 6.57 (d, J = 9.0 Hz, 1 H), 7.46-7.57 (m, 2 H) | A, 3.82 |
| 3 | 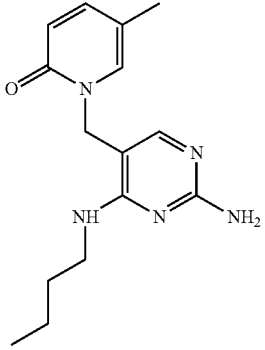 [SMILES: CCCCNc1nc(N)ncc1Cn1cc(C)ccc1=O] | $^1$H NMR (400 MHz, METHANOL-$d_4$) δ ppm 0.94 (t, J = 7.4 Hz, 3 H), 1.27-1.40 (m, 2 H), 1.55-1.65 (m, 2 H), 2.14 (s, 3 H), 3.49 (t, J = 7.0 Hz, 2 H), 4.97 (s, 2 H), 6.60 (d, J = 9.3 Hz, 1 H), 7.50 (dd, J = 9.2, 2.4 Hz, 1 H), 7.58 (s, 1 H), 7.91 (s, 1 H) | A, 3.84 |
| 4 | 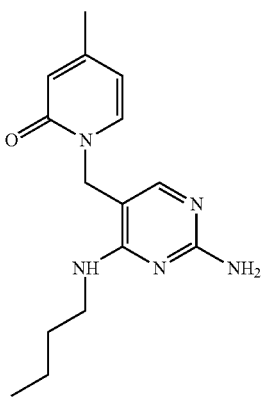 [SMILES: CCCCNc1nc(N)ncc1Cn1ccc(C)cc1=O] | $^1$H NMR (400 MHz, METHANOL-$d_4$) δ ppm 0.95 (t, J = 7.4 Hz, 3 H), 1.35 (dd, J = 14.9, 7.4 Hz, 2 H), 1.52-1.62 (m, 2 H), 2.25 (s, 3 H), 3.36 (t, J = 7.0 Hz, 2 H), 4.91 (s, 2 H), 6.37 (dd, J = 7.0, 2.0 Hz, 1 H), 6.45 (s, 1 H), 7.57 (d, J = 7.0 Hz, 1 H), 7.82 (s, 1 H) | A, 3.98 |
| 5 | 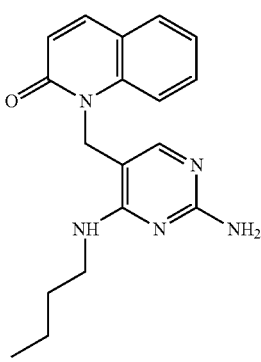 [SMILES: CCCCNc1nc(N)ncc1Cn1c(=O)ccc2ccccc21] | $^1$H NMR (400 MHz, METHANOL-$d_4$) δ ppm 0.98 (t, J = 7.4 Hz, 3 H), 1.34-1.47 (m, 2 H), 1.67 (quin, J = 7.4 Hz, 2 H), 3.53-3.60 (m, 2 H), 5.34 (s, 2 H), 6.78 (d, J = 9.5 Hz, 1 H), 7.34-7.42 (m, 1 H), 7.51 (s, 1 H), 7.58 (d, J = 8.5 Hz, 1 H), 7.65-7.73 (m, 1 H), 7.79 (d, J = 7.8 Hz, 1 H), 8.05 (d, J = 9.3 Hz, 1 H) | A, 4.29 |

TABLE 1-continued

Compounds of formula (I).

| Co. No. | STRUCTURE | H NMR | LC Method, Rt (minutes) |
|---|---|---|---|
| 6 | 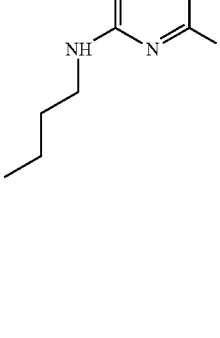 | $^1$H NMR (400 MHz, METHANOL-$d_4$) δ ppm 0.96 (t, J = 7.3 Hz, 3 H), 1.37 (sxt, J = 7.5 Hz, 2 H), 1.58-1.69 (m, 2 H), 3.53 (t, J = 7.0 Hz, 2 H), 5.09 (s, 2 H), 6.45-6.53 (m, 1 H), 7.46 (t, J = 8.3 Hz, 1 H), 7.66 (br. s., 1 H), 7.95 (br. s., 1 H) | A, 3.26 |
| 7 | 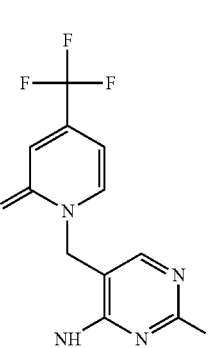 | $^1$H NMR (400 MHz, METHANOL-$d_4$) δ ppm 0.92 (t, J = 7.4 Hz, 3 H), 1.33 (dq, J = 15.0, 7.4 Hz, 2 H), 1.55 (quin, J = 7.2 Hz, 2 H), 3.36 (t, J = 6.9 Hz, 2 H), 4.97 (s, 2 H), 6.61 (dd, J = 7.3, 2.0 Hz, 1 H), 6.88 (s, 1 H), 7.84 (s, 1 H), 7.89 (d, J = 7.3 Hz, 1 H) | A, 4.33 |
| 8 | 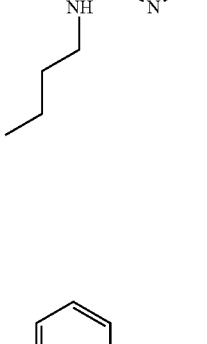 | $^1$H NMR (400 MHz, METHANOL-$d_4$) δ ppm 0.91 (t, J = 7.0 Hz, 3 H), 1.18-1.40 (m, 4 H), 1.59 (quin, J = 7.2 Hz, 2 H), 3.35-3.39 (m, 2 H), 4.96 (s, 2 H), 6.48 (td, J = 6.8, 1.3 Hz, 1 H), 6.63 (d, J = 9.0 Hz, 1 H), 7.57 (ddd, J = 9.0, 6.8, 2.0 Hz, 1 H), 7.71 (dd, J = 6.8, 1.8 Hz, 1 H), 7.85 (s, 1 H), exchangable protons not seen. | A, 4.12 |

TABLE 1-continued

Compounds of formula (I).

| Co. No. | STRUCTURE | H NMR | LC Method, Rt (minutes) |
|---|---|---|---|
| 9 | 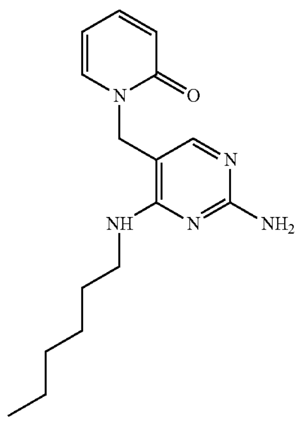 [SMILES: CCCCCCNc1nc(N)ncc1Cn1ccccc1=O] | $^1$H NMR (400 MHz, METHANOL-$d_4$) δ ppm 0.87-0.95 (m, 3 H), 1.28-1.37 (m, 6 H), 1.53-1.64 (m, 2 H), 3.37 (t, J = 7.0 Hz, 2 H), 4.96 (s, 2 H), 6.45-6.54 (m, 1 H), 6.63 (d, J = 9.0 Hz, 1 H), 7.57 (ddd, J = 9.0, 6.8, 2.0 Hz, 1 H), 7.71 (dd, J = 6.8, 1.5 Hz, 1 H), 7.85 (s, 1 H) | A, 4.47 |
| 10 | 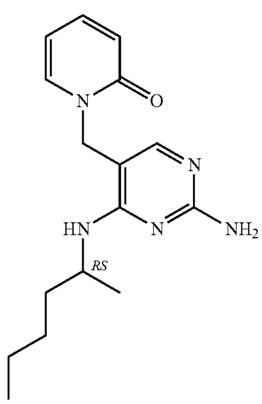 [SMILES: CCCCC(C)Nc1nc(N)ncc1Cn1ccccc1=O] | $^1$H NMR (400 MHz, METHANOL-$d_4$) δ ppm 0.86 (t, J = 7.2 Hz, 3 H), 1.09-1.17 (m, 3 H), 1.17-1.35 (m, 4 H), 1.46-1.57 (m, 2 H), 4.11-4.22 (m, 1 H), 4.79-4.87 (m, 1 H), 5.03-5.11 (m, 1 H), 6.49 (t, J = 6.8 Hz, 1 H), 6.63 (d, J = 9.0 Hz, 1 H), 7.57 (ddd, J = 9.0, 6.8, 2.0 Hz, 1 H), 7.66-7.73 (m, 1 H), 7.85 (s, 1 H) | A, 4.31 |
| 11 | 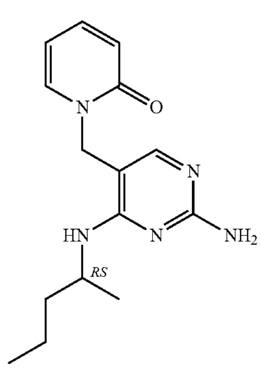 [SMILES: CCCC(C)Nc1nc(N)ncc1Cn1ccccc1=O] | $^1$H NMR (400 MHz, METHANOL-$d_4$) δ ppm 0.88 (t, J = 7.3 Hz, 3 H), 1.13 (d, J = 6.5 Hz, 3 H), 1.16-1.33 (m, 2 H), 1.39-1.63 (m, 2 H), 4.09-4.25 (m, 1 H), 4.86 (d, J = 14.8 Hz, 1 H), 5.04 (d, J = 14.8 Hz, 1 H), 6.47 (td, J = 6.8, 1.3 Hz, 1 H), 6.62 (d, J = 9.0 Hz, 1 H), 7.56 (ddd, J = 9.0, 6.8, 2.0 Hz, 1 H), 7.69 (dd, J = 6.9, 1.6 Hz, 1 H), 7.84 (s, 1 H) | A, 4.05 |

Analytical Methods. All compounds were characterized by LC-MS using the following method:

| Method A | | | |
|---|---|---|---|
| Column | YMC-PACK ODS-AQ, 50 × 2.0 mm 5 μm | | |
| Mobile Phase | A: H$_2$O (0.1%TFA) | | |
| | B: CH$_3$CN (0.05%TFA) | | |
| | Stop Time: 10 min | | |
| Gradient | TIME(min) | A% | B% |
| | 0 | 100 | 0 |
| | 1 | 100 | 0 |
| | 5 | 40 | 60 |
| | 7.5 | 40 | 60 |
| | 8 | 100 | 0 |
| Flow Rate | 0.8 mL/min | | |
| Wavelength | UV 220 nm | | |
| Oven Tem. | 50 | | |
| MS polarity | positive | | |
| LCMS | Agilent 1100 | | |

Biological Activity of Compounds of Formula (I)
Description of Biological Assays
Assessment of TLR7 and TLR8 Activity The ability of compounds to activate human TLR7 and/or TLR8 was assessed in a cellular reporter assay using HEK293 cells transiently transfected with a TLR7 or TLR8 expression vector and NFκB-luc reporter construct.

Briefly, HEK293 cells were grown in culture medium (DMEM supplemented with 10% FCS and 2 mM Glutamine). For transfection of cells in 15 cm dishes, cells were detached with Trypsin-EDTA, transfected with a mix of CMV-TLR7 or TLR8 plasmid (1700 ng), NFκB-luc plasmid (850 ng) and a transfection reagent and incubated for 48 h at 37° C. in a humidified 5% CO$_2$ atmosphere. Transfected cells were then washed in PBS, detached with Trypsin-EDTA and resuspended in medium to a density of $1.25 \times 10^5$ cells/mL. Forty microliters of cells were then dispensed into each well in 384-well plates, where 200 nL of compound in 100% DMSO was already present. Following 6 hours incubation at 37° C., 5% CO$_2$, the luciferase activity was determined by adding 15 μL of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 40 μL per well of cells transfected with the CMV-TLR7 construct alone ($1.25 \times 10^5$ cells/mL), in 384-well plates. Cell viability was measured after 6 hours incubation at 37° C., 5% CO$_2$ by adding 15 μL of ATP lite (Perkin Elmer) per well and reading on a ViewLux ultraHTS microplate imager (Perkin Elmer). Data was reported as CC$_{50}$.

In parallel, a similar dilution series of compound was used (200 nL of compound in 100% DMSO) with 40 μL per well of cells transfected with NFκB-luc reporter construct alone ($1.25 \times 10^5$ cells/mL). Six hours after incubation at 37° C., 5% CO$_2$, the luciferase activity was determined by adding 15 μl of Steady Lite Plus substrate (Perkin Elmer) to each well and readout performed on a ViewLux ultraHTS microplate imager (Perkin Elmer). Counterscreen data is reported as LEC.

Activation of ISRE Promoter Elements

The potential of compounds to induce IFN-I was also evaluated by measuring the activation of interferon-stimulated responsive elements (ISRE) by conditioned media from PBMC. The ISRE element of sequence GAAACT-GAAACT (SEQ ID NO: 1) is highly responsive to the STAT1-STAT2-IRF9 transcription factor, activated upon binding of IFN-I to their receptor IFNAR (Clontech PT3372-5W). The plasmid pISRE-Luc from Clontech (ref. 631913) contains 5 copies of this ISRE element, followed by the firefly luciferase ORF. A HEK293 cell line stably transfected with pISRE-Luc (HEK-ISREluc) was established to profile the conditioned PBMC cell culture media.

Briefly, PBMCs were prepared from buffy coats of at least two donors using a standard Ficoll centrifugation protocol. Isolated PBMCs were resuspended in RPMI medium supplemented with 10% human AB serum and $2 \times 10^5$ cells/well were dispensed into 384-well plates containing compounds (70 μL total volume). After overnight incubation, 10 μL of supernatant was transferred to 384-well plates containing $5 \times 10^3$ HEK-ISREluc cells/well in 30 μL (plated the day before). Following 24 hours of incubation, activation of the ISRE elements was measured by assaying luciferase activity using 40 μL/well Steady Lite Plus substrate (Perkin Elmer) and measured with ViewLux ultraHTS microplate imager (Perkin Elmer). The stimulating activity of each compound on the HEK-ISREluc cells was reported as LEC value, defined as the compound concentration applied to the PBMCs resulting in a luciferase activity at least two fold above the standard deviation of the assay. The LEC in turn indicates the degree of ISRE activation on transfer of a defined amount of PBMC culture medium. Recombinant interferon α-2a (Roferon-A) was used as a standard control compound.

Biological activity of compounds of formula (I). All compounds showed CC50 of >24 uM.

| # | Human TLR 7 (LEC) μM | Human TLR 8 (LEC) μM | HEK-ISRE luc (LEC) μM |
|---|---|---|---|
| 1 | 1.8 | 7.3 | 0.7 |
| 2 | 1.1 | 2.1 | 0.8 |
| 3 | 0.8 | 10.3 | 0.3 |
| 4 | 0.5 | 2.2 | 0.5 |
| 5 | 0.9 | 2.7 | 0.04 |
| 6 | 1.2 | 6.9 | 0.5 |
| 7 | 0.5 | 6.8 | 0.5 |
| 8 | 1.5 | >25 | 0.6 |
| 9 | 7.3 | >25 | 3 |
| 10 | 1.0 | 16 | 0.3 |
| 11 | 1.3 | 14.6 | 0.3 |

The invention claimed is:

1. A compound of formula (I)

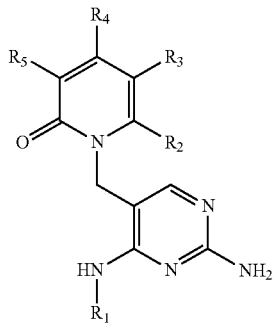

or a pharmaceutically acceptable salt, solvate or polymorph thereof, wherein $R_1$ is $C_{1-6}$ alkyl, optionally substituted by one or more substituents independently selected from the group consisting of aryl, halogen, OH, $NH_2$, $CO_2H$, $CO_2$ $C_{1-3}$alkyl, $C(O)NHC_{1-3}$alkyl, $C(O)NHSO_2C_{1-3}$alkyl, $C_{1-3}$ alkyl, $C_{3-6}$ cycloalkyl, $SO_2C_{1-3}$alkyl, $S(O)$ $C_{1-3}$alkyl, $SO_2NHC_{1-3}$alkyl, heterocyclyl and CN; and $R_2$, $R_3$, $R_4$, and $R_5$ are each independently selected from the group consisting of hydrogen, halogen, $C_{1-3}$alkyl, $C_{1-3}$alkoxy, $C_{3-6}$cycloalkyl, aryl, —$CF_3$ and heterocyclyl;

or wherein $R_2$ and $R_3$ form a 5-7 membered saturated or partially saturated monocyclic moiety optionally containing one or more heteroatoms selected from the group consisting of nitrogen, oxygen and sulfur, $R_3$ and $R_4$ form a 5-7 membered saturated or partially saturated monocyclic moiety optionally containing one or more heteroatoms selected from the group consisting of nitrogen, oxygen and sulfur, or $R_4$ and $R_5$ form a 5-7 membered saturated or partially saturated monocyclic moiety optionally comprising one or more heteroatoms selected from nitrogen, oxygen or sulfur.

2. A compound of formula (I) according to claim 1 wherein $R_1$ is n-butyl and wherein $R_2$, $R_3$, $R_4$, and $R_5$ are hydrogen.

3. A pharmaceutical composition comprising a compound according to claim 1 or a pharmaceutically acceptable salt, solvate or polymorph thereof, together with one or more pharmaceutically acceptable excipients, diluents or carriers.

4. A method of treating a disorder in which the modulation activating TLR 7 and/or TLR 8 in a cell, comprising contacting said cell with a therapeutically effective amount of at least one compound of claim 1.

5. A method of inducing interferon production in a cell, comprising contacting said cell with a therapeutically effective amount of at least one compound of claim 1.

6. A compound of formula (I) according to claim 1, wherein $R_1$ is $C_{4-6}$alkyl.

7. A compound of formula (I) according to claim 1, wherein $R_2$, $R_3$, $R_4$ and $R_5$ are each hydrogen.

8. A compound of formula (I) according to claim 1, wherein $R_2$ and $R_3$ are each independently hydrogen or $CH_3$.

9. A compound of formula (I) according to claim 1, wherein $R_4$ is $CF_3$ or $CH_3$.

10. A compound of formula (I) according to claim 1, wherein $R_5$ is F or hydrogen.

11. A compound of formula (I) according to claim 1, wherein $R_1$ is $C_{4-6}$alkyl; and $R_2$, $R_3$, $R_4$ and $R_5$ are each hydrogen.

12. A compound of formula (I) according to claim 1, wherein $R_2$ is $CH_3$; and $R_3$, $R_4$ and $R_5$ are each hydrogen.

13. A compound of formula (I) according to claim 1, wherein $R_2$, $R_4$ and $R_5$ are each hydrogen; and $R_3$ is $CH_3$.

14. A compound of formula (I) according to claim 1, wherein $R_2$, $R_3$ and $R_5$ are each hydrogen; and $R_4$ is $CF_3$ or $CH_3$.

15. A compound of formula (I) according to claim 1, wherein $R_2$, $R_3$ and $R_4$ are each hydrogen; and $R_5$ is F or hydrogen.

16. A compound of formula (I) according to claim 1, wherein $R_1$ is $C_{4-6}$ alkyl; $R_2$ is $CH_3$, and $R_3$, $R_4$ and $R_5$ are each hydrogen.

17. A compound of formula (I) according to claim 1, wherein $R_1$ is $C_{4-6}$ alkyl; $R_2$, $R_4$ and $R_5$ are each hydrogen; and $R_3$ is $CH_3$.

18. A compound of formula (I) according to claim 1, wherein $R_1$ is $C_{4-6}$ alkyl; $R_2$, $R_3$ and $R_5$ are each hydrogen; and $R_4$ is $CF_3$ or $CH_3$.

19. A compound of formula (I) according to claim 1, wherein $R_1$ is $C_{4-6}$ alkyl; $R_2$, $R_3$ and $R_4$ are each hydrogen; and $R_5$ is F or hydrogen.

20. A compound of formula (I) according to claim 1, wherein $R_1$ is selected from the group consisting of n-butyl, n-pentyl and n-hexyl.

21. A compound of formula (I) according to claim 1, wherein $R_1$ is n-butyl, and $R_2$ is $CH_3$, and $R_3$, $R_4$ and $R_5$ are each hydrogen.

22. A compound of formula (I) according to claim 1, wherein $R_1$ is n-butyl; $R_2$, $R_4$ and $R_5$ are each hydrogen; and $R_3$ is $CH_3$.

23. A compound of formula (I) according to claim 1, wherein $R_1$ is n-butyl; $R_2$, $R_3$ and $R_5$ are each hydrogen; and $R_4$ is $CF_3$ or $CH_3$.

24. A compound of formula (I) according to claim 1, wherein $R_1$ is n-butyl; $R_2$, $R_3$ and $R_4$ are each hydrogen; and $R_5$ is F or hydrogen.

25. A compound according to claim 1, wherein said compound is selected from the group consisting of

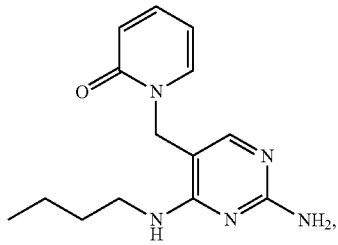

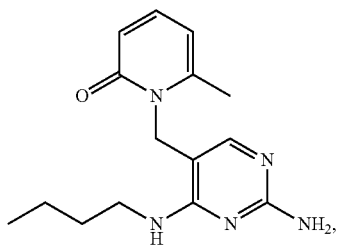

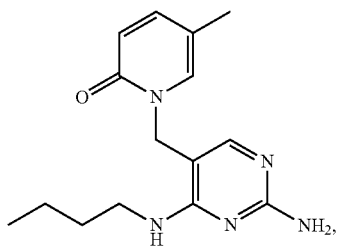

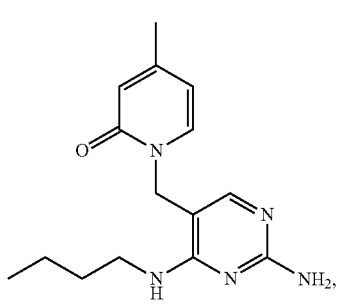

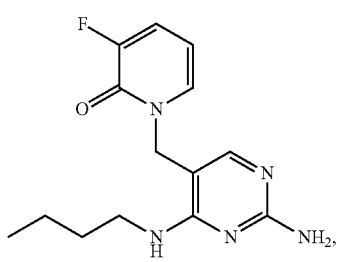

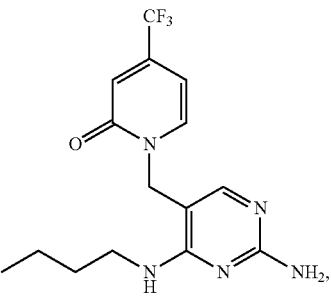

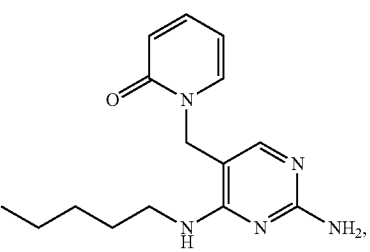

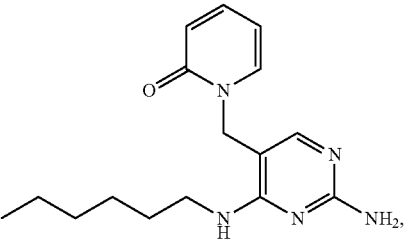

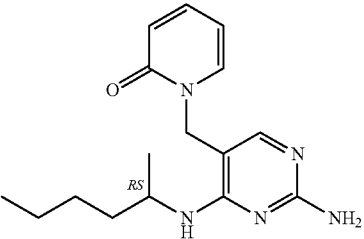 and

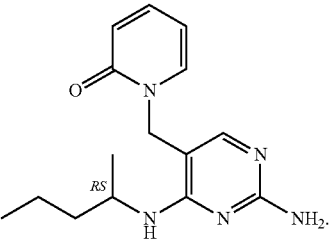

26. A method of activating TLR 7 and/or TLR 8 in a cell, comprising contacting said cell with a therapeutically effective amount of at least one compound as claimed in claim 25.

27. A method of inducing interferon production in a cell, comprising contacting said cell with a therapeutically effective amount of at least one compound as claimed in claim 25.

28. The method of claim 4, wherein the cell is in a human subject.

29. The method of claim 5, wherein the cell is in a human subject.

30. The method of claim 26, wherein the cell is in a human subject.

31. The method of claim 27, wherein the cell is in a human subject.

32. A method of preparing a compound of formula (I), said method comprising reacting a compound of formula A

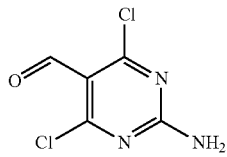

with a compound of formula A-1

to form the compound of formula B

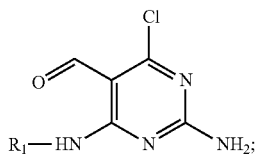

reducing the compound of formula B to form a compound of formula D

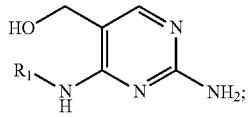

and reacting the compound of formula D with a compound of formula D-1

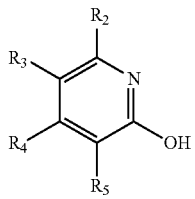

to form a compound of formula I

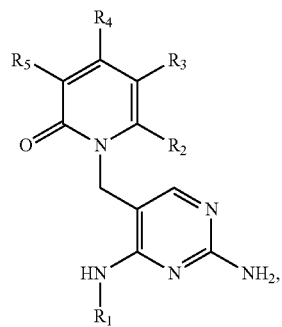

wherein $R_1$ is $C_{1-6}$ alkyl, optionally substituted by one or more substituents independently selected from the group consisting of aryl, halogen, OH, $NH_2$, $CO_2H$, $CO_2C_{1-3}$alkyl, $C(O)NHC_{1-3}$alkyl, $C(O)NHSO_2C_{1-3}$alkyl, $C_{1-3}$alkyl, $C_{3-6}$cycloalkyl, $SO_2C_{1-3}$alkyl, $S(O)C_{1-3}$alkyl, $SO_2NHC_{1-3}$alkyl, heterocyclyl and CN;

$R_2$, $R_3$, $R_4$, and $R_5$ are each independently selected from the group consisting of hydrogen, halogen, $C_{1-3}$ alkyl, $C_{1-3}$ alkoxy, $C_{3-6}$ cycloalkyl, aryl, —$CF_3$ and heterocyclyl; or $R_2$ and $R_3$ form a 5-7 membered saturated or partially saturated monocyclic moiety optionally containing one or more heteroatoms selected from the group consisting of nitrogen, oxygen and sulfur, $R_3$ and $R_4$ form a 5-7 membered saturated or partially saturated monocyclic moiety optionally containing one or more heteroatoms selected from the group consisting of nitrogen, oxygen and sulfur, or $R_4$ and $R_5$ form a 5-7 membered saturated or partially saturated monocyclic moiety optionally comprising one or more heteroatoms from nitrogen, oxygen or sulfur.

33. The method of claim 32, wherein the compound of formula B is reduced to form a compound of formula C

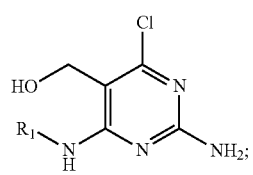

and the compound of formula C is reduced to form a compound of formula D

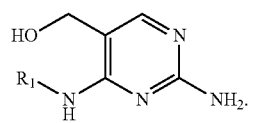

* * * * *

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaaactgaaa ct                                                         12
```